US00PP30554P3

(12) United States Plant Patent
Moon

(10) Patent No.: US PP30,554 P3
(45) Date of Patent: Jun. 4, 2019

(54) ***NYSSA SYLVATICA* PLANT NAMED 'NSMTF'**

(50) Latin Name: *Nyssa sylvatica*
Varietal Denomination: NSMTF

(71) Applicant: SOUTHERN SELECTIONS, LLC, Loganville, GA (US)

(72) Inventor: Dwayne C. Moon, Logansville, GA (US)

(73) Assignee: Southern Selections, LLC, Logansville, GA (US)

( * ) Notice: Subject to any disclaimer, the term of this patent is extended or adjusted under 35 U.S.C. 154(b) by 8 days.

(21) Appl. No.: 15/530,913

(22) Filed: Mar. 21, 2017

(65) Prior Publication Data

US 2018/0279526 P1 Sep. 27, 2018

(51) Int. Cl.
*A01H 5/04* (2018.01)
*A01H 6/00* (2018.01)

(52) U.S. Cl.
USPC ..... Plt./216
CPC ..... *A01H 6/00* (2018.05); *A01H 5/04* (2013.01)

(58) Field of Classification Search
USPC ..... Plt./216
See application file for complete search history.

*Primary Examiner* — Anne Marie Grunberg
(74) *Attorney, Agent, or Firm* — Stinson Leonard Street LLP

(57) ABSTRACT

A new and distinct variety of Black Tupelo tree named 'NSMTF' substantially as herein shown, illustrated and described, characterized particularly as to novelty by its deep, dark, lustrous foliage in summer and brilliant red leaves in the fall while having pyramidal growth habit, and a strong central leader with full scaffolding branch structure. This form difference, along with unique foliage colors makes my selection uniquely different from all known patent selections and seedlings.

8 Drawing Sheets

Latin name of genus and species: *Nyssa sylvatica.*

Varietal denomination: Black Tupelo tree which I have named 'NSMTF'.

CROSS REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The present invention relates to a new and distinct variety of Black Tupelo tree (*Nyssa sylvatica*), which I have named 'NSMTF'.

Discovery

The new *Nyssa sylvatica* is a product of chance discovery. The new variety 'NSMTF' is the result of a selection made by the inventor, Dwayne Moon, from a number of *Nyssa sylvatica* seedlings planted in the spring of 2010 in a production field in Loganville, Ga. in Walton County. Originally the seedlings were purchased in 2008 from a nursery in Florida which takes seeds collected in the wild; that is, the seeds were hand-picked from cultivated trees in cultivated field environments located in tree farms following American Nursery Standards. The seeds were mechanically harvested, graded by quality, bundled, and maintained in refrigerated conditions until shipment to the grower. After the pulp was removed, the seeds go through an acid treatment and stratification with cold temperatures for an allotted time for germination. The seeds were sowed in seed beds at the Florida nursery, maintained under raised bed cultivated conditions through the summer months in seed beds, lifted and distributed at the end of the year as *Nyssa sylvatica* bare-root seedlings. Bare-root seedlings purchased in 2008 from the Florida nursery were placed into an above-ground container operation in three gallon cultivated container conditions. In the winter of 2009, these liners were relocated from a liner field to a production field where they are maintained and cultivated under field production balled and burlapped conditions according to the American Nursery Standards and Georgia Department of Agriculture licensed monitoring. Through this process, the new *Nyssa sylvatica* 'NSMTF' was discovered as a superior seedling among a group of cultivated *Nyssa sylvatica* trees at which point it was moved into production fields in Loganville, Ga. where the claimed cultivar 'NSMTF' continues to be evaluated. Evaluation of this tree continues in a field in Washington, Ga. in Wilkes County.

Propagation

'NSMTF' was asexually propagated by the method of vegetative propagation at my direction in the summer of 2013 in Loganville, Walton County, Ga. Softwood cuttings three to five inches long were treated with 3000 ppm potassium indole-3-butyric acid (KIBA). The cuttings were then placed in peat pots filled with horticultural growing media and then intermittently misted for a period of five to six weeks. This propagation form softwood cuttings and resulting progeny have proven the characteristics of my new variety to be genetically stable. Furthermore, these observations have confirmed that my new variety represents a new and improved variety of *Nyssa sylvatica* Black Tupelo tree as particularly evidenced by the pyramidal growth habit with a strong central leader; its full scaffolding branch structure; and it has deep, dark green lustrous foliage in summer and brilliant red leaves in the fall. These genetic traits can be consistently reproduced by asexual propagation.

Uniqueness

'NSMTF' was discovered in a block of seedling Black Tupelo trees (unknown *Nyssa sylvatica* parents) purchased by Moon's Tree Farm, Inc. from a supplier of seedling liners in Florida. I claim that the genetic characteristics of this tree are the result of naturally occurring cross-pollination. Due to the nature of the seedling purchase, comparison of surrounding cross pollinators is not known. The characteristics of my new tree distinguish it from other typical seedling Black Tupelo trees and the known cultivars. At the time this tree was selected, I observed 'NSMTF' Black Tupelo tree as a 2 inch caliper tree exhibiting pyramidal growth habit with a strong central leader; it has full scaffolding branch structure; and it has deep, dark green lustrous foliage like (RHS 131A) in summer and brilliant red leaves in the fall like (RHS 42A to RHS 43A to RHS 44A). The remainder of the trees in this block had medium green foliage color with pendulous branching.

Use

'NSMTF' was observed for a period of several years and is believed to be particularly useful as a specimen tree in commercial and residential areas, for street tree planting and in large areas such as golf courses, commercial sites and parks. 'NSMTF' will also benefit growers who will profit from the desired look of a high quality tree due to its pyramidal growth habit with a strong central leader; it has full scaffolding branch structure; and it has deep, dark green lustrous foliage in summer and brilliant red leaves in the fall.

SUMMARY OF THE INVENTION

Background

Seedling black tupelo trees are somewhat pyramidal in youth and are usually not well-branched, with many of the branches being pendulous. As the trees mature, the spreading and often horizontal branches will form an irregularly rounded or flat-topped crown with great variation in mature habit. Mature native black tupelo trees are typically 30-50 feet in height with a spread of 20-30 feet; some native specimens can reach 100 feet or more in height. In nursery settings, black tupelo trees often require a significant amount of effort to maintain a central leader. My black tupelo tree 'NSMTF' is an improvement over the species in that it has a pyramidal growth habit with a strong central leader; it has full scaffolding branch structure; and it has deep, dark green lustrous foliage in summer and brilliant red leaves in the fall.

Black tupelo tree is native to the eastern United States from Maine, central Michigan to southern Florida and to east Texas. It grows in a variety of sites from the creek bottoms of the southern coastal plains to 3,000 foot high ridges in North Carolina. This variety grows best in well-drained, light-textured soils on low ridges of second bottoms and on high flats of silty alluvium, preferring lower slopes and terraces in the Southeastern United States. In upland areas it grows best in the loams and clay loams of lower slopes and coves. It has a slow to medium growth rate with 12 to 15 feet over a 10 to 15 year period with a typical height of 30 to 50 feet and 20 to 30 feet spread. It has a medium green leaf in summer changing to yellow to orange to scarlet to purple colors in the fall. My new cultivar differs from the species in that it is asexually reproduced with pyramidal growth habit with a strong central leader; it has full scaffolding branch structure; and it has deep, dark green lustrous foliage in summer and brilliant red leaves in the fall. The ultimate height and width of 'NSMTF' is not known. I expect my new variety of black tupelo tree 'NSMTF' to perform as well as the species.

Industry Representation

Cultivated black tupelo tree is predominantly represented in the industry by seedling material reproduced sexually through seed production and seedling establishment with some cultivars. This accounts for a high degree of variability in the industry, both in the landscape and nursery. Seedling black tupelo tree is variable in growth rate, habit, and leaf characteristics, and overall consistency is difficult to maintain in a production system.

The *Manual of Woody Landscape Plants* lists eighteen black tupelo cultivars. Of these, only the following are similar to the present cultivar 'NSMTF' in that they have red fall color: *Nyssa sylvatica* 'NXSXF' U.S. Plant Pat. No. 11,391 Forum™ (hereinafter referred to as "Forum™"), *Nyssa sylvatica* 'Miss Scarlet' (hereinafter referred to as "Miss Scarlet"), *Nyssa sylvatica* 'Hayman Red' Red Rage® (hereinafter referred to as "Red Rage®"), 'Red Red Wine' (hereinafter referred to as "Red Red Wine"), *Nyssa sylvatica* 'Wildfire' (hereinafter referred to as "Wildfire"), and 'Wisley Bonfire' (hereinafter referred to as "Wisley Bonfire"). Also popular in the industry are the following new cultivars of black tupelo trees which are *Nyssa sylvatica* 'David Odum' Afterburner® Tupelo (hereinafter referred to as "Afterburner®"), *Nyssa sylvatica* 'PRP1' Fire Master™ (hereinafter referred to as "Fire Master™"), *Nyssa sylvatica* 'JFS-Red1' Firestarter® (hereinafter referred to as "Firestarter®"), *Nyssa sylvatica* 'Nsuhh' Green Gable™ (hereinafter referred to as "Green Gable™"; U.S. Plant Pat. No. 22,951), *Nyssa sylvatica* 'JFS-PN Legacy1' Gum Drop® (hereinafter referred to as "Gum Drop®"), and *Nyssa sylvatica* 'WFH1' Tupelo Tower™ (hereinafter referred to as "Tupelo Tower™"; U.S. Plant Pat. No. 22,976). Forum™ has a dominant leader with conical habit. The present cultivar 'NSMTF' differs from Forum™ in that 'NSMTF' has a dominant central leader with a pyramidal habit. There is no mention of the growth habit of Miss Scarlet or Red Red Wine. Red Rage® is pyramidal but becoming more rounded with age. The present cultivar 'NSMTF' differs from Miss Scarlet, Red Red Wine, and Red Rage® in that 'NSMTF' has a dominant central leader with a pyramidal habit. Wildfire has a conical growth habit or sometimes flat-topped crown with many slender nearly horizontal branches. The present cultivar 'NSMTF' differs from Wildfire in that 'NSMTF' has a dominant central leader with a pyramidal habit. Afterburner® has an upright pyramidal to oval habit with bright green, glossy leaves. The present cultivar 'NSMTF' differs from Afterburner® in that 'NSMTF' has a 15 dominant central leader with a pyramidal habit along with deep, dark green lustrous foliage like (RHS 131A). Firemaster™ has a broadly pyramidal habit but lacks a dominant central leader; therefore, the present cultivar 'NSMTF' differs from Firemaster® in that 'NSMTF' has a dominant central leader with a pyramidal habit. Firestarter® has a narrow oval habit with a dominant central leader. The present cultivar 'NSMTF' differs from Firestarter® in that 20 'NSMTF has a pyramidal shape with a dominant central leader. Green Gable™ has upwardly sweeping lateral branches forming a pyramidal habit with glossy dark green leaves like (RHS147A) in the summer. The present cultivar 'NSMTF' differs from Green Gable™ in that 'NSMTF has a pyramidal shape with a dominant central leader and a deep, dark green lustrous foliage like (RHS 131A). Gum Drop® has a compact, upright oval habit. The present cultivar 'NSMTF' differs from Gum Drop® in that 'NSMTF has a pyramidal shape with a dominant central leader. Tupelo Tower™ has an upright columnar habit. The present cultivar 'NSMTF' differs from Tupelo Tower™ in that 'NSMTF' has a pyramidal shape with a dominant central leader. The present cultivar 'NSMTF' differs from the aforementioned 5 varieties in that 'NSMTF' has the most deep, dark, lustrous foliage in summer and brilliant red leaves in the fall while having pyramidal growth habit, and a strong central leader with full scaffolding branch structure. This form difference, along with unique foliage colors makes my selection uniquely different from all known patent selections and seedlings.

BRIEF DESCRIPTION OF THE DRAWINGS

The accompanying photographs depict the color of the tree and foliage of my new black tupelo tree as nearly as is reasonably possible to make the same in a color illustration of this character.

DETAILED DESCRIPTION OF THE INVENTION

Botanical Description of the Plant

Figure 1:
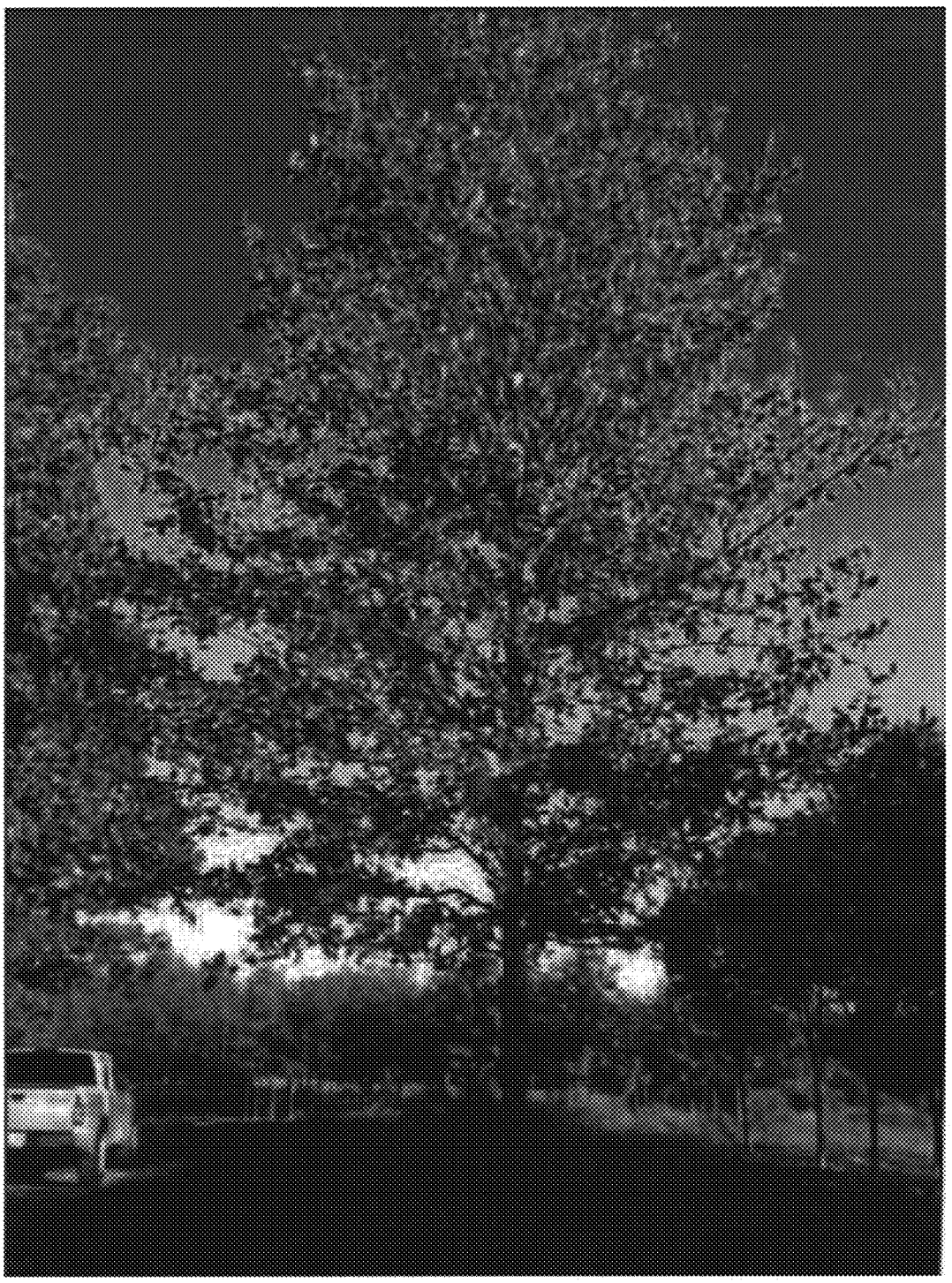
FIG. 1 taken in the production field of Walton County, Loganville, Ga. in October 2013 shows the claimed cultivar.
Figure 2:
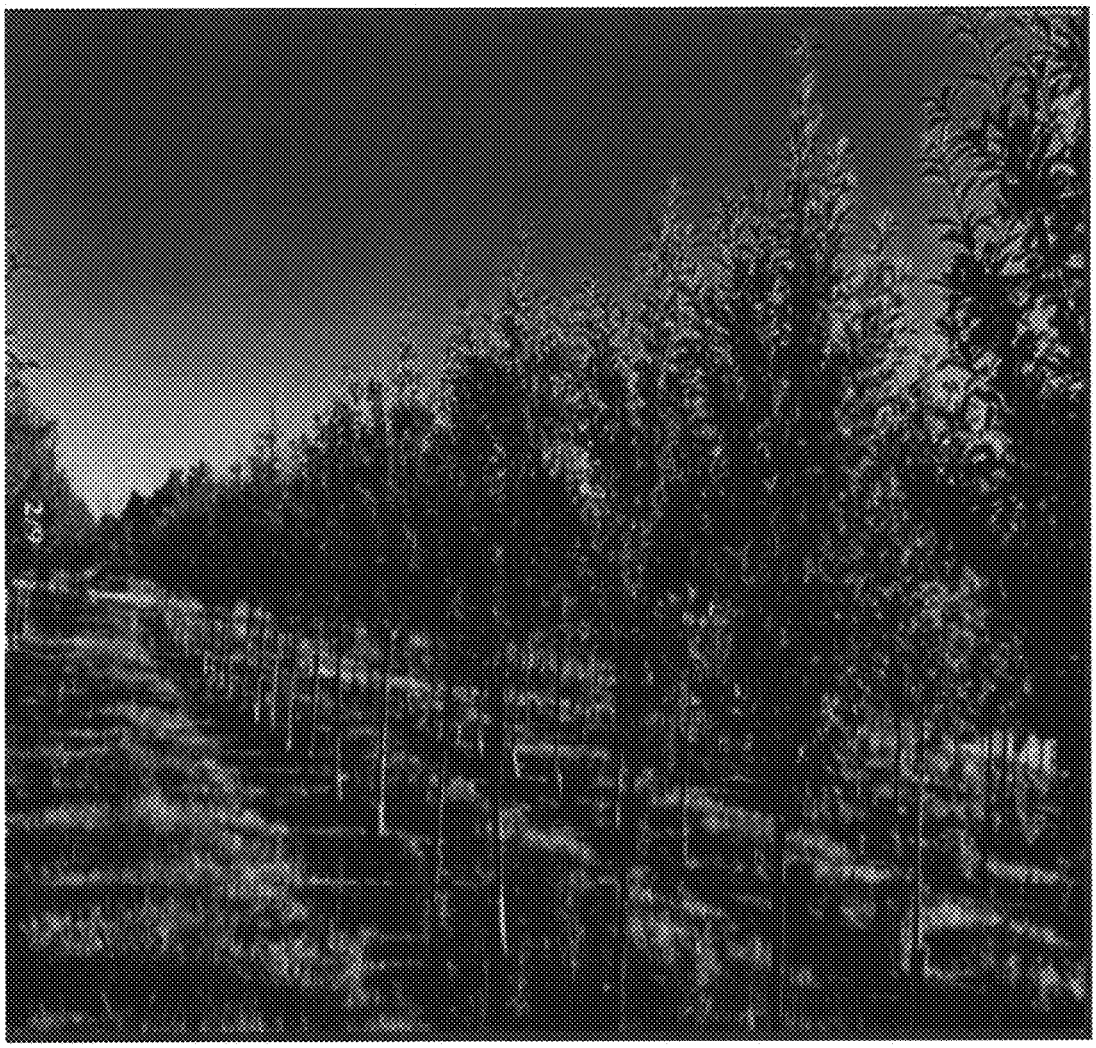
FIG. 2 taken of a field block shows the progeny of my new variety.
Figure 3:
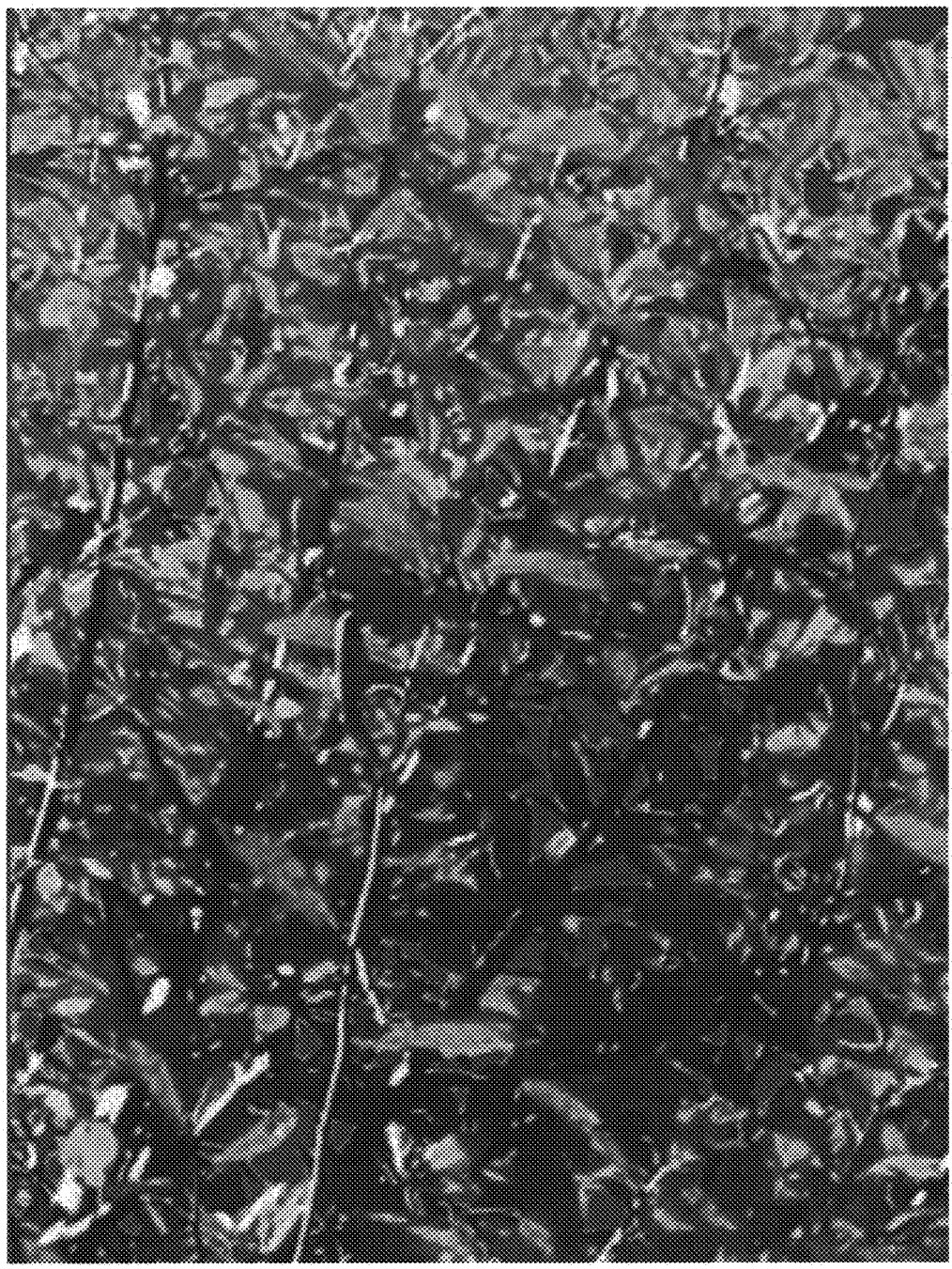
FIG. 3 shows the overall fall color of the claimed cultivar.
Figure 4:
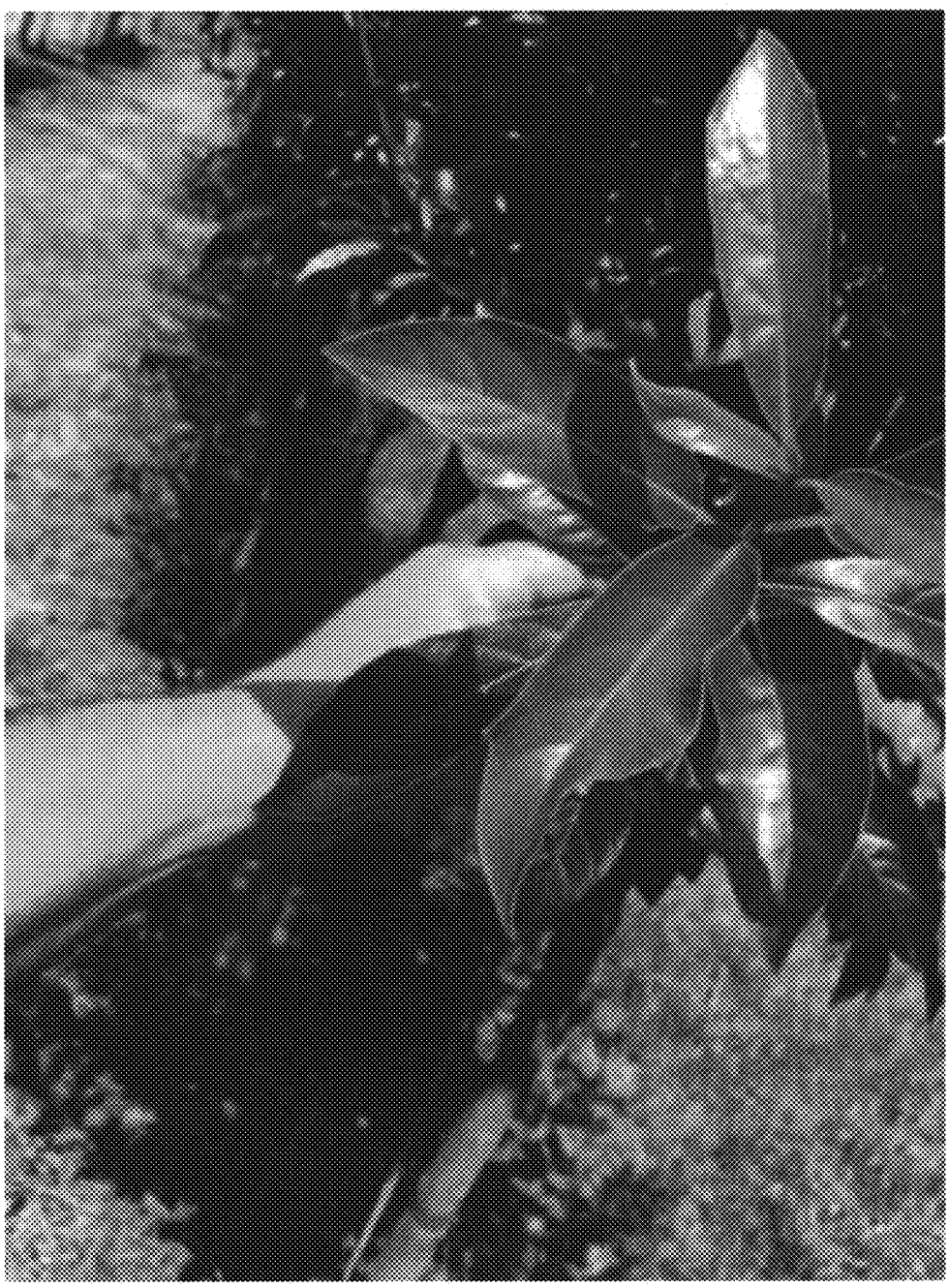
FIG. 4 shows the summer foliage of my new variety.
Figure 5:
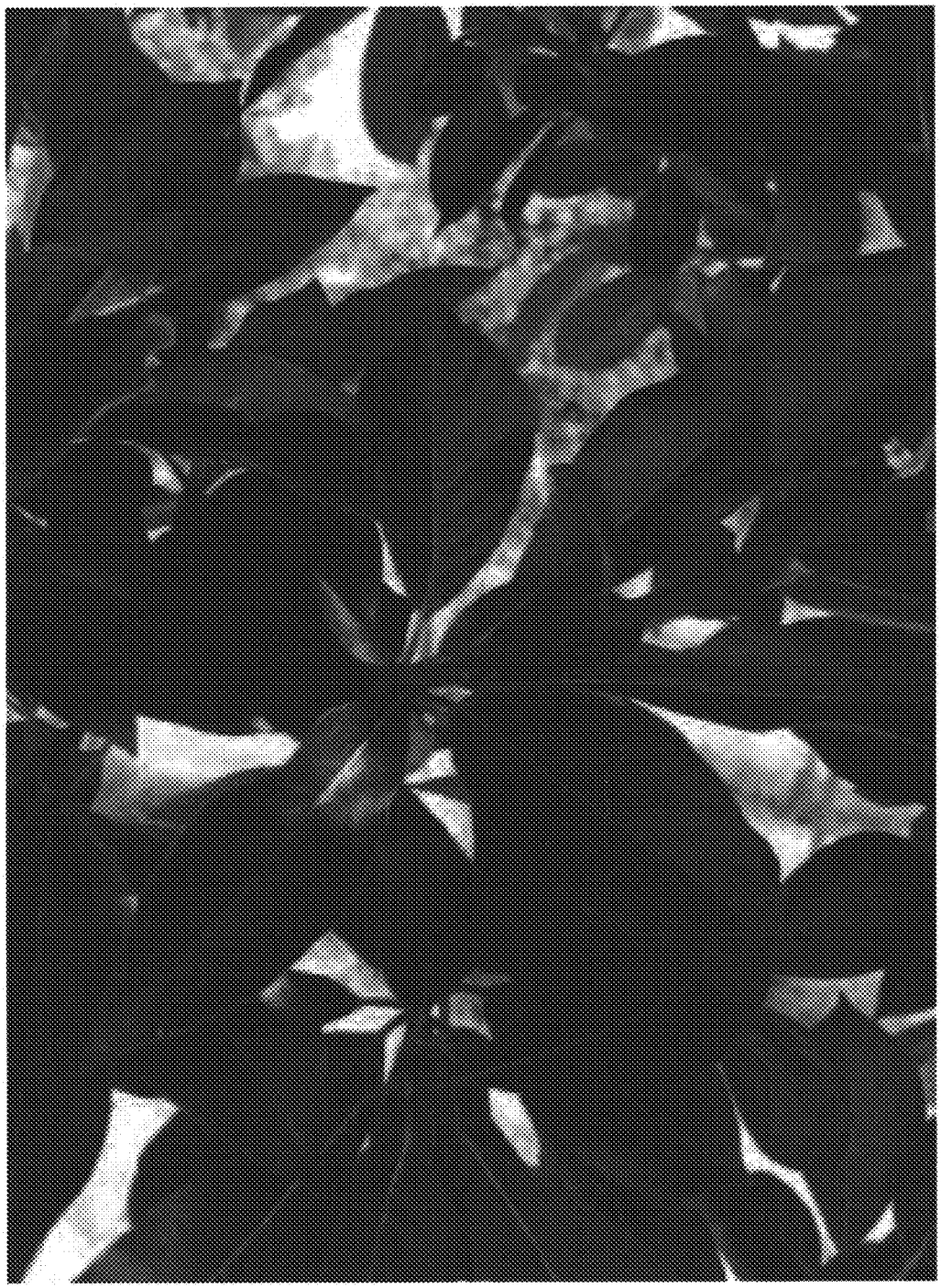
FIG. 5 shows the new growth foliate of my new variety.
Figure 6:
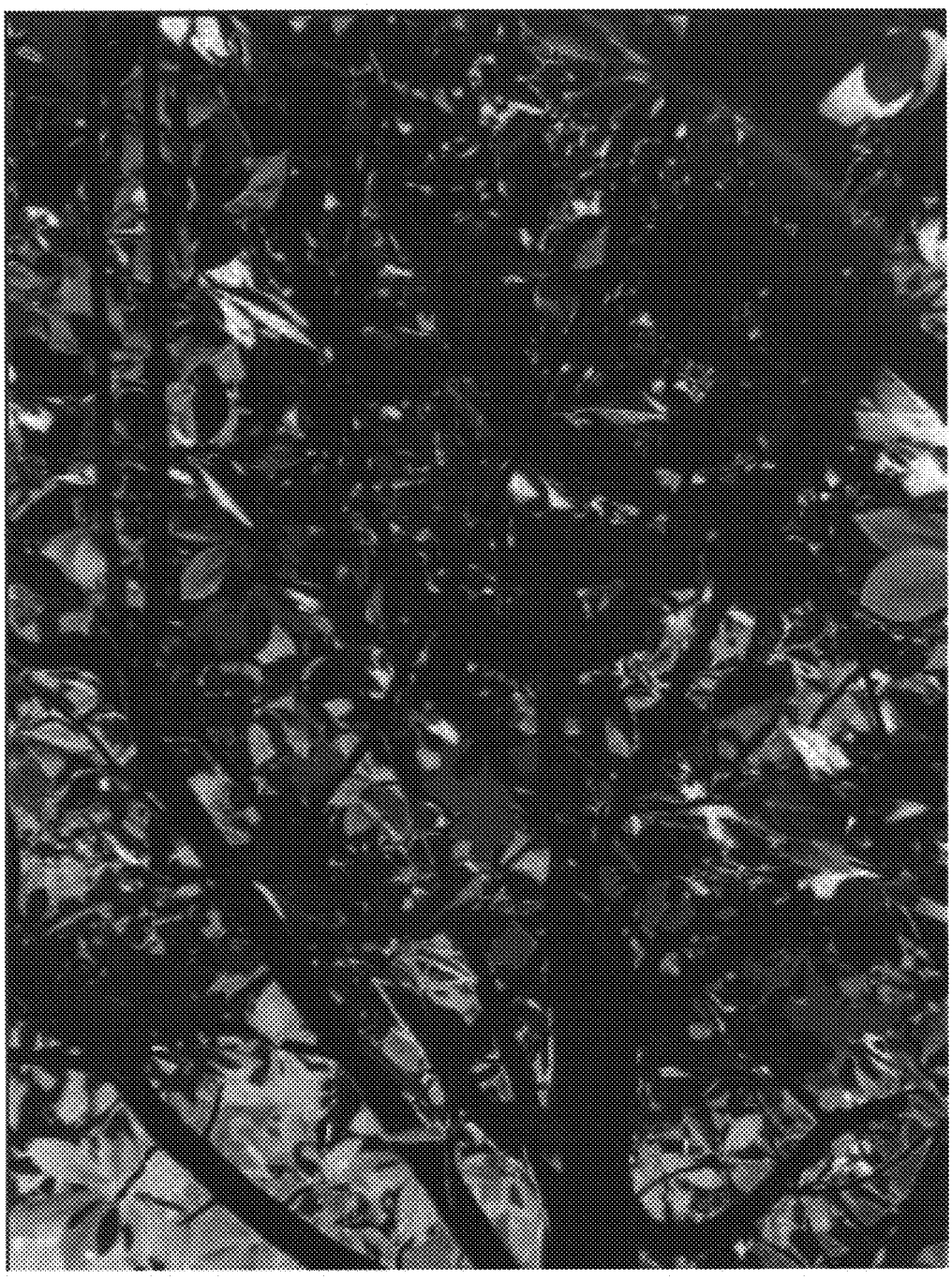
FIG. 6 shows the strong central leader and pyramidal growth habit of my new variety.
Figure 7:
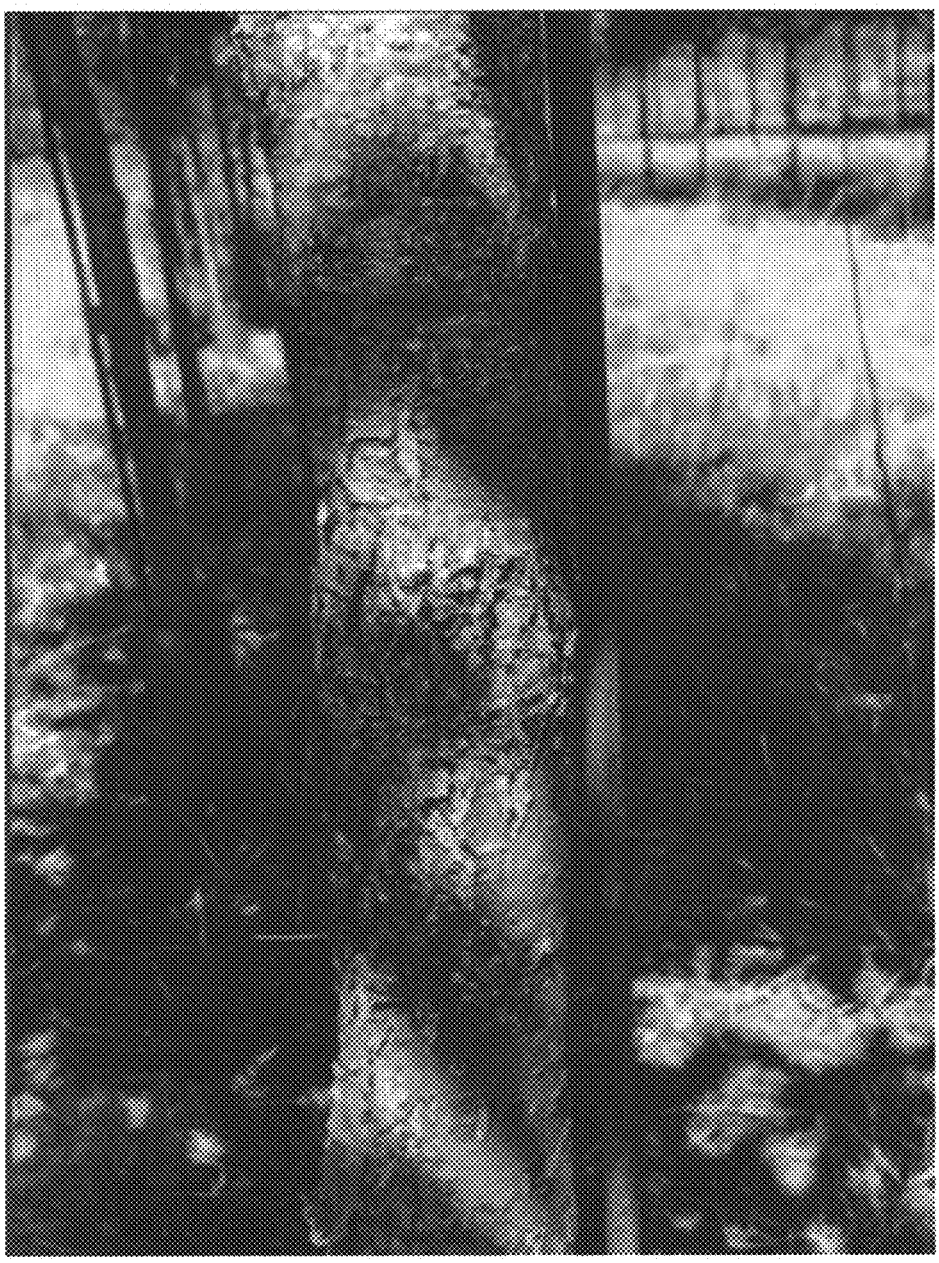
FIG. 7 shows the trunk and bark of my new variety.
Figure 8:
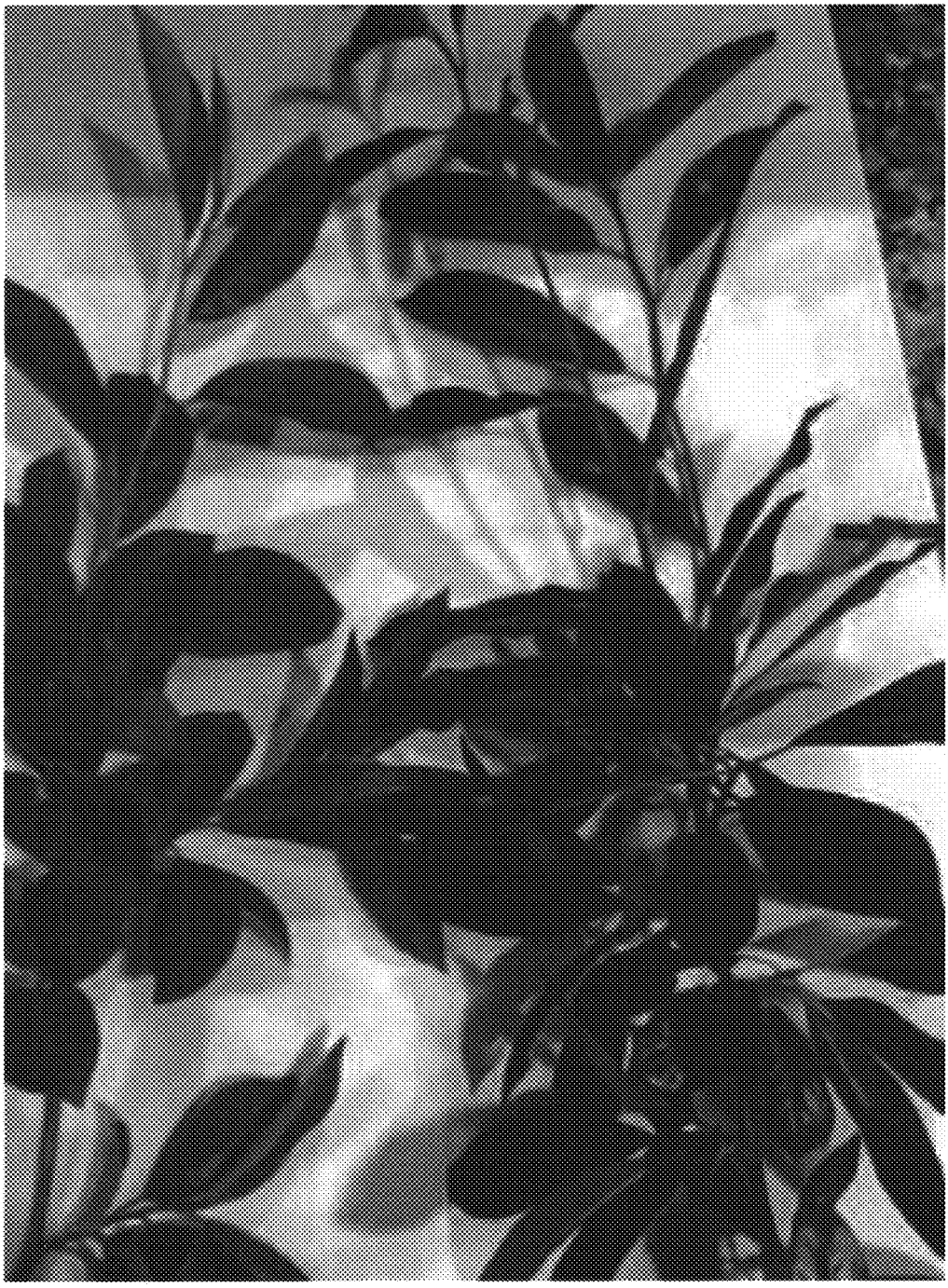
FIG. 8 shows the side by side foliage comparison of the deep, dark green lustrous foliage of the seedling of the claimed cultivar compared to the lighter green of the seedling black tupelo tree.

The following is a detailed description of 'NSMTF' Black Tupelo tree with color terminology in accordance with The Royal Horticulture Society (R.H.S.) Colour Chart except where the context indicates a term having its ordinary dictionary meaning.

The named cultivar has not been observed under all growing conditions, and variations may occur as a result of different growing conditions. All progeny of my new variety, insofar as have been observed by the inventor, have remained genetically stable in all characteristics described hereinafter. Other than as set out hereinafter, as of this time, no other characteristics have been observed by the inventor different from common Black Tupelo trees.

Scientific name: *Nyssa sylvatica* 'NSMTF'.

Parentage: Naturally occurring cross-pollinated seedlings of unknown origin, black tupelo tree growing in a cultivated area in Washington, Ga.

Propagation:

*Root description*.—The named cultivar is grafted onto seedling rootstocks, so the root system is expected to be typical of the species, which is somewhat coarse.

Tree:

*Growth habit*.—Pyramidal with full scaffolding branch structure and a strong central leader.

*In a container or in the ground*.—In ground.

*Height*.—Approximately 30 foot at 5 years.

*Plant spread*.—Approximately 15 foot at 5 years.

*Growth rate*.—Height to width ratio 2-1. Average caliper growth rate between ¾ to 1 inch per year.

*Trunk diameter*.—Approximately 7 inch caliper measured at 12 inches above the ground at 5 years. Rises through the canopy and maintains a central leader.

*Trunk*.—Trunk bark texture: Ridged with furrowed characteristics. Trunk bark color: greyed-green like (RHS 188C).

Leaves:

*Arrangement*.—Alternate.

*Type*.—Simple.

*Sheen*.—Satiny to slightly glossy.

*Shape of leaf blade*.—Ovate.

*Leaf apex shape*.—Acuminate.

*Leaf base shape*.—Cuneate.

*Leaf margin characteristics*.—Entire.

*Description of any leaf pubescence*.—None.

*Leaf length*.—7.5 cm to 10 cm.

*Leaf width*.—2.5 cm to 4 cm.

*Leaf internode length*.—About 3.2 cm.

*Leaf venation description*.—Pinnate.

*Petiole length*.—1 cm to 2.5 cm.

*Petiole diameter*.—2.9 mm.

*Petiole color*.—Green like (RHS 145A).

*Overall shape*.—Ovate.

*Margin*.—Smooth.

*Tip*.—Acuminate.

*Base*.—Cuneate.

*Spring leaf color*.—First emerging leaves are yellow green like (RHS N144B).

*Summer leaf color*.—Upper leaf surface is a deep, dark green lustrous foliage like (RHS 131A) while the lower leaf surface is greyed-green like (RHS 138B). The center vein is yellow green like (RHS 146C).

*Fall color*.—Fall color red like (RHS 42A to RHS 43A to RHS 44A).

*Pubescence*.—Glabrous.

Flowers:

*Overall*.—The tree is dioecious and has only male flowers. About ten to twelve small flowers are borne in head-like, globose racemes. These globose racemes average 16 mm in diameter.

*Shape*.—Individually, each flower is a very small whorl of stamens.

*Size*.—Individual flowers have an average diameter of 8 mm.

*Color*.—Yellow-green like (RHS 145A to RHS 145B.

*Petals*.—None observed.

*Sepals*.—About eight sepals arranged in a single whorl. Length: About 1 mm. Width: About 0.5 mm. Shape: Ovate. Apex: Acute; reflexing. Margin: Entire. Texture, upper and lower surfaces: Smooth, glabrous. Color: yellow-green like (RHS 145A) to (RHS 145B).

*Stamen*.—About eight to ten per flowers. Filament length: About 2 mm to 3 mm by 0.5 mm in diameter. Filament color is yellow-green like (RHS 154B).

*Anthers*.—Broadly oval but slightly irregular in shape, 1.0 mm long by 0.7 mm to 0.9 mm in diameter. Color is yellow-green like (RHS 154B).

*Pollen*.—Yellow like (RHS 10B).

*Pedicel*.—Length 4 mm to 5 mm; diameter 0.5 mm; color yellow-green like (RHS 144B).

*Peduncle*.—1 cm to 2 cm long by 0.5 mm to 0.8 mm diameter.

*Fragrance*.—None.

*Flowering season*.—Flowering in early to mid-April.

*Flower longevity on plant*.—Individual flowers last about ten days to two weeks on the plant; flowers not persistent.

Buds:

*Terminal flower buds*.—Length: about 5.9 mm. Diameter: about 4.1 mm. Color: Brown like (RHS 200A). Texture: Smooth, glabrous.

*Lateral flower bud*.—Length: About 4.4 mm. Diameter: about 2.9 mm. Color: Brown like (RHS 200A). Texture: Smooth, glabrous.

Fruit: Subglobose to ellipsoid, medium green like (RHS 138B) 3 cm long and 2 cm wide, cone-like aggregate with separate pointed carpels, each with two dark red seeds like (RHS 44B).

OTHER CHARACTERISICS

Pathogen and pest resistance: Trees of the new *Nyssa* have been not observed to be resistant to pathogens and pests common to *Nyssa* trees.

Temperature tolerance: Trees of the new *Nyssa* have been observed to tolerate high temperatures about 40.5° C. and low temperatures about −18.9° C. when grown in USDA Hardiness Zone 6. The new variety is suitable for growing in USDA zones 4 through 9.

What is claimed is:

1. A new and distinct variety of Black Tupelo tree named 'NSMTF' substantially as herein shown, illustrated and described, characterized particularly as to novelty by its deep, dark, lustrous foliage in summer and brilliant red leaves in the fall while having pyramidal growth habit, and a strong central leader with full scaffolding branch structure.

* * * * *